(12) United States Patent
Jayaraman et al.

(10) Patent No.: US 11,639,391 B2
(45) Date of Patent: May 2, 2023

(54) STABLE LIQUID PHARMACEUTICAL COMPOSITION

(71) Applicant: DR. REDDY'S LABORATORIES LIMITED, Hyderabad (IN)

(72) Inventors: Murali Jayaraman, Kancheepuram (IN); Pravin Nair, Mumbai (IN); Navneet Kaur, Ludhiana (IN); Deepak Thumbrahalli, Kampli (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 16/604,031

(22) PCT Filed: Apr. 18, 2018

(86) PCT No.: PCT/IN2018/050230
§ 371 (c)(1),
(2) Date: Oct. 9, 2019

(87) PCT Pub. No.: WO2018/193471
PCT Pub. Date: Oct. 25, 2018

(65) Prior Publication Data
US 2021/0101987 A1 Apr. 8, 2021

(30) Foreign Application Priority Data
Apr. 18, 2017 (IN) .............................. 201741013746

(51) Int. Cl.
*A61K 39/395* (2006.01)
*C07K 16/28* (2006.01)
*A61K 47/26* (2006.01)
*C07K 16/32* (2006.01)

(52) U.S. Cl.
CPC .......... *C07K 16/2866* (2013.01); *A61K 47/26* (2013.01); *C07K 16/32* (2013.01); *C07K 2317/94* (2013.01)

(58) Field of Classification Search
None
See application file for complete search history.

(56) References Cited

U.S. PATENT DOCUMENTS

2008/0071063 A1\* 3/2008 Allan ................. C07K 16/2866
530/387.1
2015/0071925 A1 3/2015 Larson et al.
2017/0189528 A1 7/2017 Kaya et al.

FOREIGN PATENT DOCUMENTS

WO 2008066322 A1 6/2008
WO 2017122121 A1 7/2017

OTHER PUBLICATIONS

Actemra product information, p. 1-40, (Year: 2010).\*
International Search Report dated Jun. 20, 2018, for corresponding International Patent Application No. PCT/IN2018/050230.
Written Opinion dated Jun. 20, 2018, for corresponding International Patent Application No. PCT/IN2018/050230.

\* cited by examiner

*Primary Examiner* — Yunsoo Kim
(74) *Attorney, Agent, or Firm* — Pergament & Cepeda LLP; Milagros A. Cepeda; Edward D. Pergament

(57) ABSTRACT

The present invention provides a stable liquid formulation of an antibody in phosphate-amino acid based dual buffer system. The antibody formulated in phosphate-amino acid based dual buffer system imparts optimum stability to the antibody, at lower as well as higher concentrations. Further, the antibody formulated in phosphate-amino acid based buffer system has low viscosity and is suitable for therapeutic administration of high concentrations of antibody.

8 Claims, 3 Drawing Sheets

STABLE LIQUID PHARMACEUTICAL COMPOSITION

This application is a National Stage Application under 35 U.S.C. § 371 of PCT International Application No. PCT/IN2018/050230, filed Apr. 18, 2018, which takes priority from Indian Provisional Application Number IN 201741013746, filed Apr. 18, 2017, all of which are herein incorporated by reference in their entirety.

FIELD OF INVENTION

The present invention relates to a stable liquid antibody formulation, wherein the antibody is formulated in a dual buffer system comprising 'phosphate-amino acid buffer'.

BACKGROUND

Advances in biotechnology have paved the way for the development of a large number of antibodies for therapeutic use. However, for any antibody therapeutics, stability of the antibody formulation is one of the most important criteria for ensuring its safety, as well as its effective administration.

Liquid protein/antibody formulations are generally preferred due to their convenience in administration, and suitability in administering with many commercially available devices. However antibodies being larger and more complex, as compared to traditional "small molecule" drugs, are also more unstable in solution. Antibodies are more sensitive to pH, temperature and oxidation, and can undergo a variety of covalent and non-covalent, modifications and/or degradations in solution. In particular, degradation of an antibody is faster in liquid formulations, which leads to physical and chemical instability of the molecule. Examples of chemical instability include, deamidation, hydrolysis, oxidation or disulfide exchange, whereas physical instability can be a result of denaturation, aggregation, adsorption or precipitation.

Further, liquid formulations with high antibody/protein concentrations exhibit high viscosity and increased aggregation in solution, affecting the stability and efficacy of the molecule. Thus, antibodies in liquid/solution pose inherent challenges to formulate for therapeutic uses.

The objective of the present invention is to address these challenges in the development of stable antibody formulations.

SUMMARY

The present invention discloses a stable liquid antibody formulation, wherein the formulation comprises a dual buffer system comprising phosphate and amino acid as the buffer.

Components. The amino acid component in the dual buffer system is the counter ion to the phosphate component. The said 'phosphate-amino acid' dual buffer system enables stabilization of antibody in the concentration range of from about 10 mg/ml to about 200 mg/ml. In particular, the invention discloses a stable liquid formulation in phosphate-amino acid buffer, comprising sorbitol, surfactant, and optionally arginine.

Specifically, the above said inventive formulation is devoid of any known anti-oxidant/s. In other words, the inventive formulation composition protects the antibody (e.g, tocilizumab) from oxidation, even without the use of any known anti-oxidant/s in the composition.

In addition, the present invention discloses a stable liquid antibody formulation of low viscosity, wherein the formulation comprises 'phosphate-amino acid' buffer system and wherein the viscosity of the formulation is less than 10 cP, and preferably less than 5 cP.

Further, the antibody formulated in 'phosphate-amino acid' buffer system is stable upon following storage conditions such as at 2-8° C. for at least 6 months or at 25° C. for at least 6 months, or at 40° C. for at least 2 weeks or at 40° C. for at least 4 weeks.

The aggregate content in the antibody composition formulated in the 'phosphate-amino acid' based buffer system is less than 5% and monomeric content is at least 95% under above mentioned storage conditions.

BRIEF DESCRIPTION OF DRAWINGS

FIG. 1 illustrates size exclusion chromatography (SEC data), the effect of various buffers on the HMW and monomer content of tocilizumab (230 mg/ml) formulations prepared as per example 1.

DETAILED DESCRIPTION OF THE INVENTION

Definitions

Figure 1A:
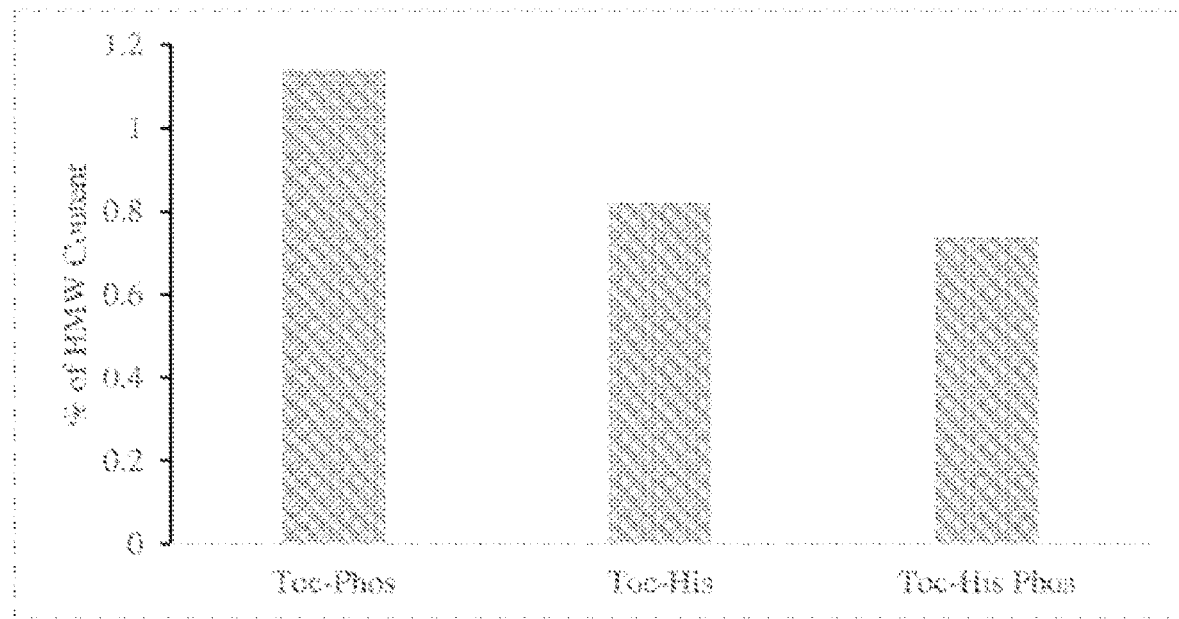
FIG. 1(a) represents HMW content.

The term "antibody" refers to a glycoprotein comprising at least two heavy (H) chains and two light (L) chains inter-connected by disulfide bonds, or an antigen-binding portion thereof. The "antibody" as used herein encompasses whole antibodies or any antigen binding fragment (i.e., "antigen-binding portion") or fusion protein thereof.

The term "stable" formulation refers to the formulation wherein the antibody therein retains its physical stability and/or chemical stability and/or biological activity upon storage.

The term "anti-oxidant" mentioned herein the invention includes, an agent which inhibits oxidation and thus is used to prevent the deterioration of preparations by the oxidative process. Such compounds include by way of example and without limitation, methionine, cysteine, carnosine ascorbic acid, ascorbyl palmitate, citric acid, butylated hydroxyanisole, butylated hydroxytoluene, hydrophosphorous acid, monothioglycerol, propyl gallate, methionine, sodium ascorbate, sodium citrate, sodium sulfide, sodium sulfite, sodium bisulfite, sodium formaldehyde sulfoxylate, thioglycolic acid, sodium metabisulfite, EDTA (edetate), pentetate. The disclosed formulation of the invention is devoid of anti-oxidant, in particular methionine.

Stability studies provides evidence of the quality of an antibody under the influence of various environmental factors during the course of time. ICH's "Q1A: Stability Testing of New Drug Substances and Products," states that data from accelerated stability studies can be used to evaluate the effect of short-term excursions higher or lower than label storage conditions that may occur during the shipping of the antibodies.

Various analytical methods are available for measuring the physical and chemical degradation of the antibody in the pharmaceutical formulations. An antibody "retains its physical stability" in a pharmaceutical formulation if it shows substantially no signs of aggregation, precipitation and/or denaturation upon visual examination of color and/or clarity, or as measured by UV light scattering or by size exclusion chromatography. An antibody is said to "retain its chemical stability" in a pharmaceutical formulation when its shows no or minimal formation of product variants which may include variants as a result of chemical modification of antibody of interest such as deamination, oxidation etc. Analytical methods such as ion exchange chromatography and hydrophobic ion chromatography may be used to investigate the chemical product variants.

The term 'monomer' as used herein describes antibodies consisting of two light chains and two heavy chains. The monomer content of an antibody composition is typically analyzed by size exclusion chromatography (SEC). As per the separation principle of SEC the large molecules or molecules with high molecular weight (HMW) elute first followed by smaller or lower weight molecules. In a typical SEC profile for an antibody composition, aggregates that may include dimers, multimers, etc., elute first, followed by monomer, and the clipped antibody variants or degradants may be eluted last. In some circumstances the aggregate peak or the degradant peaks may not elute as a baseline separated peaks but instead as a shoulder or abnormal broad peaks. In order to maintain the appropriate activity of an antibody, in particular of a therapeutic antibody, it is desirable to reduce the formation of aggregate or degradant products and hence control the monomer content to a target value. Ability to inhibit the formation of aggregate and degradant content as measured at various time points during stability studies may indicate the suitability of the candidate formulation for antibody of interest. TSK-GEL G3000SWXL (7.8 mm×30 cm) column from TOSCH can be used on water HPLC to perform SEC.

The term 'main peak' as used herein refers to the peak that elutes in abundance (major peak) during a cation exchange chromatography. The peak that elutes earlier than the main peak, during a cation exchange chromatography, with a charge that is acidic relative to the main peak is termed acidic variant peak. The peak that elutes later than the main peak, during a cation exchange chromatography, with a charge that is relatively basic than the main peak is termed as basic variant peak. The main peak content can be determined by Ion exchange chromatography (IEC). There are two modes of IEC available viz., cation and anion exchange chromatography. Positively charged molecules bind to anion exchange resins while negatively charged molecules bind to cation exchange resins. In a typical cation exchange chromatographic profile of an antibody composition acidic variants elute first followed by the main peak and thereafter lastly the basic variants will be eluted. The acidic variants are result of antibody modifications such as deamidation of asparagine residues. The basic variants are result of incomplete removal of C-terminal lysine residue(s), incomplete cyclization of N-terminal glutamine, isomerization of asparagine, and also notably, oxidation of methionine residues present in Fc region of an antibody [Chromatographic analysis of the acidic and basic species of recombinant monoclonal antibodies; mAbs; Page number 581; Volume 4; Issue 5]. In general, in an antibody a lysine residue is present at the C-terminal end of both heavy and light chain. An antibody molecule containing lysine at both heavy and light chain is referred to as K2 variant, the antibody molecule containing lysine residue at either one of heavy and light chain is referred to as K1 variant and antibody molecule having none is K0 molecule. Carboxypeptidase B (CP-B enzyme) enzyme acts on the C-terminal lysine residues present on K2 and K1 variants and thus converting them as K0 molecules. As per circumstances of the case, the IEC analysis can be carried out for samples digested with carboxypeptidase B (CP-B) enzyme. In a typical stability study it is expected that a stable formulation leads to reduction in formation of charge variants (acidic and basic variants), during the study, and hence minimize any reduction in main peak content.

Dynamic light scattering (DLS) measures time-dependent fluctuations in the scattering intensity arising from particles undergoing random Brownian motion. Diffusion coefficient and particle size information can be obtained from the analysis of these fluctuations. More specifically, the method provides the ability to measure size characteristics of proteins in a liquid medium. The diffusion coefficient values obtained from this technique are directly proportional to the solubility of the molecule in a given solution.

Differential Scanning Fluorimetry (DSF) allows rapid determination on the stability of proteins in high throughput, and allows to compare directly different proteins or the same protein under different conditions to be studied. DSF monitors thermal unfolding of proteins in the presence of a fluorescent dye and is typically performed by using a real-time PCR instrument. The fluorescent dyes that can be used for DSF are highly fluorescent in a non-polar environment, such as the hydrophobic sites on unfolded proteins, compared to aqueous solution where the fluorescence is quenched. The fluorescence intensity is plotted as a function of temperature; this generates a sigmoidal curve that can be described by a two-state transition.

The term "percentage recovery" refers to the proportion of the antibody concentration obtained in the final formulation buffer to the antibody concentration in the process buffer, which precedes the formulation step. For example, the process buffer can be the elution or filtration buffer of the downstream process step that precedes the formulation step.

The high concentration formulation for an antibody refers to a formulation, which enables higher dose to be administered to a subject using a low volume, which is equal to, or less than the formulation for standard treatment.

Pharmaceutically acceptable excipients refer to the additives or carriers, which may contribute to stability of the antibody in formulation. The excipients may encompass stabilizers and tonicity modifiers. Examples of stabilizers and tonicity modifiers include, but not limited to, sugars, polyols, salts, amino acids or surfactants, and derivatives and combination thereof.

Sugars and polyols can be referred to monosaccharides, disaccharides, and polysaccharides.

Examples of sugars include, but are not limited to, sucrose, trehalose, glucose, dextrose, raffinose and others. Additionally, polyol refers to an alcohol containing multiple hydroxyl groups. Examples of polyols include, but are not limited to, mannitol, sorbitol, and others.

Surfactant refers to pharmaceutically acceptable excipients used to protect the protein formulations against various stress conditions, like agitation, shearing, exposure to high temperature etc. The suitable surfactants include but are not limited to polyoxyethylensorbitan fatty acid esters such as Tween 20™ or Tween 80™, polyoxyethylene-polyoxypropylene copolymer (e.g. Poloxamer, Pluronic), sodium dodecyl sulphate (SDS) and the like or combination thereof.

Salts are used as tonicity modifiers and examples of salts include but not limited to sodium chloride, potassium chloride, magnesium chloride, arginine hydrochloride, sodium thiocyanate, ammonium thiocyanate, ammonium sulfate, ammonium chloride, calcium chloride, zinc chloride and/or sodium acetate.

One or more amino acids may also be part of an antibody formulation as stabilizer and can be selected from a basic amino acids or hydrophobic amino acids or a combination thereof Certain specific aspects and embodiments of the invention are more fully described by reference to the following examples. However, these examples should not be construed as limiting the scope of the invention in any manner.

DETAILED DESCRIPTION OF THE EMBODIMENTS

The present invention discloses a stable liquid antibody formulation comprising a dual buffer system comprising phosphate and amino acid as the buffer components. The 'phosphate-amino acid' based dual buffer system is suitable for formulating antibody at low, as well as high concentrations. Further, the buffer system enables the formulation to be of less viscous, even at high concentrations of the antibody. In addition, the disclosed buffer is advantageous in terms of "better recovery" of the antibody vis a vis the "formulation process". This process, following antibody purification, involves, first, a "buffer-exchange" step, in which the buffer of the last downstream process step is exchanged with the buffer that the antibody intents to be formulated in. But this "exchange" step is often accompanied by considerable loss in antibody. However when the "downstream buffer" is exchanged with the "phosphate-amino acid" buffer of the present invention, this antibody loss is significantly reduced.

An embodiment of the invention discloses a stable liquid antibody formulation, wherein the formulation comprises a phosphate-amino acid dual buffer system.

In the above said embodiment of the invention, the amino acid component in the said buffer system acts as a counterion to the phosphate component of the buffer.

In a further embodiment of the invention, the amino acid is selected from the group consisting of basic amino acid and hydrophobic amino acid.

In a further embodiment, the basic amino acid is selected from histidine, lysine and arginine; the hydrophobic amino acid can be glycine or alanine.

In an embodiment, the invention discloses a stable liquid antibody formulation, wherein the antibody is formulated in a phosphate-amino acid buffer system, and wherein the concentration of the antibody ranges from about 10 mg/ml to about 200 mg/ml.

In an embodiment, the invention discloses a stable liquid, high concentration antibody formulation, wherein the antibody is formulated in a phosphate-amino acid buffer system, and wherein the concentration of the antibody is at least 20 mg/ml, or at least 50 mg/ml, or at least 100 mg/ml or at least 150 mg/ml.

In an embodiment, the invention discloses a stable liquid antibody formulation of, low viscosity, wherein the formulation comprises a phosphate-amino acid buffer system and wherein the viscosity of the formulation is less than 10 cP, preferably less than 5 cP. The formulation may include pharmaceutically acceptable salts, wherein the concentration of the salts and/or the buffering agents are less than 100 mM, preferably less than 50 mM.

In any of the above-mentioned embodiments, the antibody formulated in a phosphate-amino acid buffer remains stable under at least one of following storage conditions such as at 2-8° C. for at least 6 months or at 25° C. for at least 6 months or at 40° C. for at least 2 weeks, or at 40° C. for at least 4 weeks.

In an embodiment, the invention discloses a stable liquid antibody formulation, wherein the formulation comprises a phosphate-amino acid dual buffer system wherein the formulation is devoid of anti-oxidant/s.

In any of the above-mentioned embodiments of the invention, the antibody is a therapeutic antibody.

In the above-mentioned embodiment, the therapeutic antibody is anti-IL6R antibody or anti-HER2 antibody.

In an embodiment, the invention discloses a stable pharmaceutical formulation of anti-IL6R antibody in phosphate-amino acid buffer, comprising sorbitol, and surfactant.

In the above mentioned embodiment, the anti-IL6R antibody is devoid of any anti-oxidant/s.

In an embodiment, the invention discloses a stable pharmaceutical formulation of anti-IL6R antibody in phosphate-amino acid buffer, comprising sorbitol and surfactant, and wherein, the formulation is devoid of any anti-oxidant/s.

In yet another embodiment, the invention discloses a stable pharmaceutical formulation of anti-IL6R antibody in phosphate-amino acid buffer, comprising sorbitol, surfactant and arginine, and wherein, the formulation is devoid of any anti-oxidant/s.

In any of the above mentioned embodiments, the said anti-oxidant is methionine.

In an embodiment, the invention discloses a stable liquid tocilizumab formulation, wherein the formulation comprises a phosphate-amino acid buffer system. The said phosphate-amino acid buffer is preferably a phosphate-histidine, phosphate-glycine or a phosphate-aspartate buffer.

In an embodiment, the invention discloses a stable liquid tocilizumab formulation, wherein the antibody is formulated in a phosphate-amino acid buffer system, and wherein the concentration of the antibody ranges from about 20 mg/ml to about 180 mg/ml.

In the above-mentioned embodiments, tocilizumab formulated in phosphate-amino acid buffer, remains stable under at least one of following storage conditions, such as at 2-8° C. for at least 6 months or at 25° C. for at least 6 months or at 40° C. for at least 2 weeks, or at 40° C. for at least 4 weeks.

In another embodiment, the invention discloses a stable liquid formulation of tocilizumab comprising a phosphate-amino acid buffer system, wherein the formulation maintains at least 95% of monomeric content of the antibody composition, under at least one of following storage conditions, such as at 2-8° C. for at least 6 months or at 25° C. for at least 6 months or at 40° C. for at least 2 weeks, or at 40° C. for at least 4 weeks.

In yet another embodiment, the invention discloses a stable liquid formulation of tocilizumab comprising a phosphate-amino acid buffer system, wherein the formulation contains less than 5% aggregate content of the antibody composition, under at least one of following storage conditions, such as at 2-8° C. for at least 6 months or at 25° C. for at least 6 months or at 40° C. for at least 2 weeks, or at 40° C. for at least 4 weeks.

In another embodiment, the invention discloses a stable liquid formulation of tocilizumab comprising a phosphate-amino acid buffer system, wherein the formulation maintains at least about 50% of tocilizumab in main peak content, under at one of the following storage conditions such as at 2-8° C. for at least 3 months or at 25° C. for at least 3 months or at 40° C. for at least 2 weeks or at 40° C. for at least 4 weeks.

In the above mentioned embodiment of the invention, the stable tocilizumab formulation in phosphate-amino acid buffer comprises less than 10% of basic variants of the antibody in the formulation, under at one of the following storage conditions such as at 2-8° C. for at least 3 months or at 25° C. for at least 3 months or at 40° C. for at least 2 weeks, or at 40° C. for at least 4 weeks. Basic variants of an antibody are result of incomplete removal of C-terminal lysine residue(s), incomplete cyclization of N-terminal glutamine, isomerization of asparagine, and also notably, oxidation of methionine residues present in Fc region of an antibody.

In an embodiment, the invention discloses a stable liquid formulation of tocilizumab comprising phosphate-histidine buffer, sorbitol and surfactant.

In an embodiment, the invention discloses a stable liquid formulation of tocilizumab comprising phosphate-histidine buffer, sorbitol, surfactant and arginine wherein, the formulation is devoid of methionine.

In the above mentioned embodiment, the antibody is stable even after multiple freeze-thaw cycles. Sorbitol present in the formulation protects/stabilizes the antibody during multiple freeze-thaw stress conditions.

In the above mentioned embodiment, the concentration of tocilizumab stabilized by sorbitol in phosphate-histidine buffer ranges from about 20 mg/ml to about 200 mg/ml.

In an embodiment, the invention discloses a stable liquid formulation of trastuzumab, wherein the formulation comprises a phosphate-amino acid buffer system.

Further, in any of the above-mentioned embodiments, the formulation may include pharmaceutically acceptable excipients such as sugars, polyols, surfactants, salts, amino acids and combinations and derivatives thereof. Preferably, the polyol is sorbitol.

EXAMPLES

Tocilizumab suitable for storage in the present pharmaceutical composition is produced by standard methods known in the art. For example, tocilizumab is prepared by recombinant expression of immunoglobulin light and heavy chain genes in a mammalian host cell such as Chinese Hamster Ovary cells. Further, the expressed tocilizumab is harvested and the crude harvest is subjected to standard downstream process steps that include purification, filtration and optionally dilution or concentration steps. For example, the crude harvest of tocilizumab may be purified using standard chromatography techniques such as affinity chromatography, ion-exchange chromatography and combinations thereof. The purified tocilizumab solution can additionally be subjected to one or more filtration steps, and the solution obtained is subjected to further formulation studies.

Example-1

Single Buffer Vs Phosphate-Amino Acid Dual Buffer

Figure 1B:
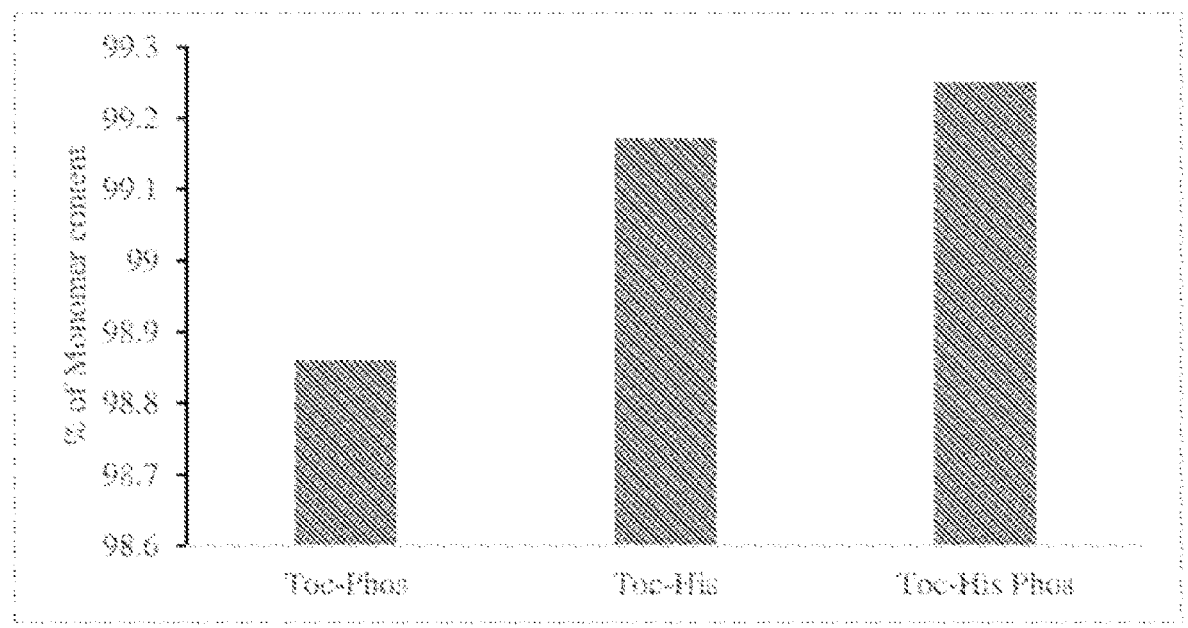
FIG. 1(b) represents monomer content.
Figure 2:
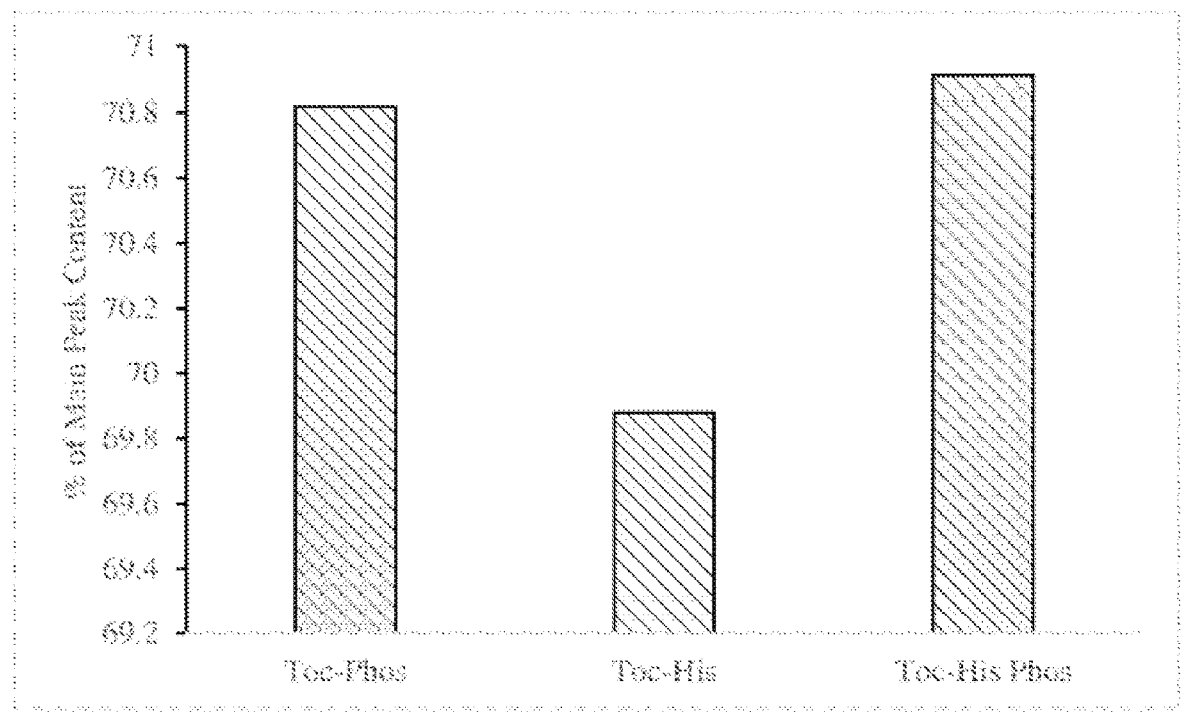
FIG. 2 illustrates ion exchange chromatography (IEX) data, the effect of various buffers on the main peak content of tocilizumab (230 mg/ml) formulations prepared as per example 1.

Tocilizumab (at concentration 35 mg/ml) obtained from final step of downstream process, was buffer exchanged and concentrated up to 230 mg/ml in single buffers as well as dual buffer such as phosphate-amino acid. Details of the buffer compositions are given in Table 1. After concentrating tocilizumab in different buffers up to 230 mg/ml, the samples were checked for high molecular weight (HMW) species, and monomer content using size exclusion chromatography [results are shown in FIG. 1 (a) and (b)]. And also checked for main peak content using ion exchange chromatography [results are shown in FIG. 2].

TABLE 1

Buffer compositions used in example 1

| Buffer composition | Final pH |
|---|---|
| 20 mM Phosphate Buffer | 6.0 |
| 20 mM Histidine buffer | 6.0 |
| 20 mM Phosphate-Histidine buffer | 6.0 |

Example-2

Formulations of High Concentration Tocilizumab (180 mg/ml) in Phosphate-Amino Acid Based Dual Buffer System To achieve a stable liquid, high concentration formulation of tocilizumab as part of experimental design various 'phosphate-amino acid' based dual buffer combinations were prepared in 20 mM concentrations. Tocilizumab (at concentration 30.02 mg/ml) obtained from final step of downstream process, was buffer exchanged into various phosphate-amino acid dual buffers (listed in Table-2) and concentrated to 180 mg/ml in the said dual buffers. Tocilizumab composition buffer exchanged with histidine buffer is maintained as control, since the approved and marketed formulations of 180 mg/ml of tocilizumab, Actemra® or RoActemra®, are in histidine buffer. Additionally, one of the dual buffers is kept as 'non-phosphate-amino acid' based buffer so as to serve as a negative control.

Percentage recovery of tocilizumab in various buffers (post buffer exchange and concentration) were calculated, and details of the same are provided in Table-2.

TABLE 2

Percentage of recovery of tocilizumab 180 mg/ml formulations prepared as per Example-2

| Tocilizumab (180 mg/ml) in a buffer composition (20 mM) | % of recovery |
|---|---|
| Histidine buffer (control) | 89.5 |
| Phosphate-Histidine | 95.7 |
| Phosphate-Aspartate | 96.0 |
| Phosphate-Succinate | 90.0 |
| Succinate-Glycine | 80.2 |

Viscosity of all the 'phosphate-amino acid' based dual buffer formulations was measured and observed to be below 5 cP.

Example 3

Solubility Measurements of Tocilizumab Using Dynamic Light Scattering (DLS)

To understand the solubility pattern of tocilizumab in various buffer backgrounds, tocilizumab sample (at concentration 30.02 mg/ml) from the downstream process step were buffer exchanged into various buffer compositions, as listed in Table-3, and concentrated to 140-180 mg/ml. Tocilizumab at high concentrations were then serially diluted to lower concentrations. The samples were then subjected to DLS to measure the diffusion co efficient, which is indicative of solubility of tocilizumab. Results of the same are represented in Table-3.

TABLE 3

DLS data of tocilizumab (140-180 mg/ml) formulations as per Example-3

| Buffer Composition | Tocilizumab concentration (mg/ml) | Diffusion co-efficient (cm$^2$/s) |
|---|---|---|
| Histidine buffer (Control) | 179.5 | 3.00E−07 |
| | 59.8 | 5.50E−07 |
| | 29.9 | 5.80E−07 |
| | 15.0 | 5.40E−07 |
| Phosphate-Histidine | 142.0 | 3.50E−07 |
| | 47.3 | 4.90E−07 |
| | 23.7 | 4.60E−07 |
| | 11.8 | 4.60E−07 |
| Phosphate-Aspartate | 163.9 | 3.50E−07 |
| | 54.6 | 4.90E−07 |
| | 27.3 | 5.20E−07 |
| | 13.7 | 4.90E−07 |
| Phosphate-Succinate | 148.3 | 3.50E−07 |
| | 49.4 | 4.90E−07 |
| | 24.7 | 4.60E−07 |
| | 12.4 | 4.60E−07 |
| Phosphate-Glycine | 179.9 | 2.90E−07 |
| | 60.0 | 4.70E−07 |
| | 30.0 | 5.30E−07 |
| | 15.0 | 5.20E−07 |
| Succinate-Glycine | 183.2 | 2.60E−07 |
| | 61.1 | 4.00E−07 |
| | 30.5 | 4.90E−07 |
| | 15.3 | 4.70E−07 |

Example-4

Accelerated Stability Studies

Tocilizumab sample (at concentration 30.02 mg/ml) from the downstream process step were buffer exchanged into various buffer compositions, as listed in Table-3, and concentrated to 180 mg/ml. These samples were then subjected for accelerated stability studies wherein the tocilizumab formulations in the respective buffer backgrounds were stored at 40° C. for 2 weeks. Post storage, the samples were analyzed for high molecular weight (HMW) species and monomer content [results are shown in Table-4] using size exclusion chromatography (SEC). And, acidic species, main peak content of the samples [results are shown in Table-5] were analyzed using ion-exchange chromatography (IEX).

TABLE 4

SEC data of tocilizumab (180 mg/ml) formulations, formulated according to Example-4, and stored at 40° C. for 2 weeks

| Buffer composition (20 mM) | % HMW at 40° C. at 2 weeks | % of monomer at 40° C. at 2 weeks |
|---|---|---|
| Histidine buffer (control) | 3.7 | 96.9 |
| Phosphate-Histidine | 3.2 | 96.6 |
| Phosphate-Aspartate | 4.1 | 95.6 |
| Phosphate-Succinate | 4.1 | 95.6 |
| Phosphate-Glycine | 4.6 | 95.1 |
| Succinate-Glycine | 9.0 | 90.5 |

TABLE 5

IEX data of tocilizumab (180 mg/ml) formulations, formulated according to Example-4, and stored at 40° C. for 2 weeks

| Buffer composition (20 mM) | % of acidic species at 40° C. at weeks | % of main peak content at 40° C. at 2 weeks |
|---|---|---|
| Histidine buffer (control) | 30.0 | 58 |
| Phosphate-Histidine | 30.9 | 58 |
| Phosphate-Aspartate | 30.0 | 58 |
| Phosphate-Succinate | 31.4 | 60 |
| Phosphate-Glycine | 30.0 | 60 |
| Succinate-Glycine | 59.6 | 34 |

Example 5

Figure 3:
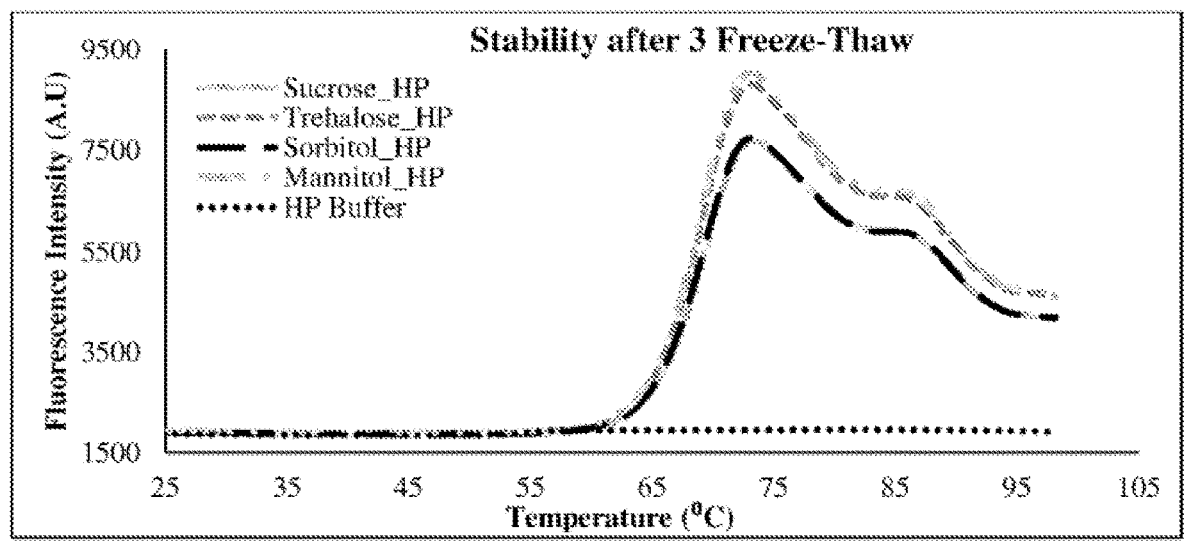
FIG. 3 illustrates differential scanning fluorimetry (DSF) data, the effect of various sugars on the stability of tocilizumab post freeze-thaw studies.

Selection of Appropriate Sugar to Stabilize Tocilizumab Using Differential Scanning Fluorimetry To understand, the thermal unfolding nature of tocilizumab using DSF technique, tocilizumab (20 mg/ml) was formulated in histidine-phosphate buffer (HP) back ground and was spiked with various sugars. Post which, all samples were subjected for multiple (at least 3) freeze-thaw cycles by freezing the samples to −80° C. using a deep freezer and thawed at room temperature. The samples were analyzed using DSF. Results are represented in FIG. 3.

Example-6

Formulations of Tocilizumab (180 mg/ml) in Phosphate-Amino Acid Based Dual Buffer System Comprising Different Excipients As part of experimental design, to evaluate role of different excipients in stabilizing tocilizumab at high concentration, tocilizumab which was obtained from downstream chromatographic step was concentrated to 180 mg/ml in phosphate-histidine buffer back ground. Post which, various excipients such as polyol (sorbitol), amino acids (methionine/arginine), tonicity modifier (sodium chloride) and surfactant (polysorbate 80) were added in different concentrations and in different combinations. Details of the formulations are given in Table 6. FDA approved subcutaneous formulation of tocilizumab containing histidine buffer, arginine, methionine and polysorbate hass used as reference standard in subsequent experiment. Post which, all samples were subjected for accelerated stability studies at 25° C. for 6 months and 40° C. for 4 weeks. The samples were periodically withdrawn at different time points and analyzed for change in pH [results are shown in Table 7], visual inspection [results are shown in Table 8], monomer, HMW content and LMW content [results are shown in Table 9 a-c] using SEC analysis. And also, the samples were tested for real time stability studies at 2-8° C.

Figure 4:
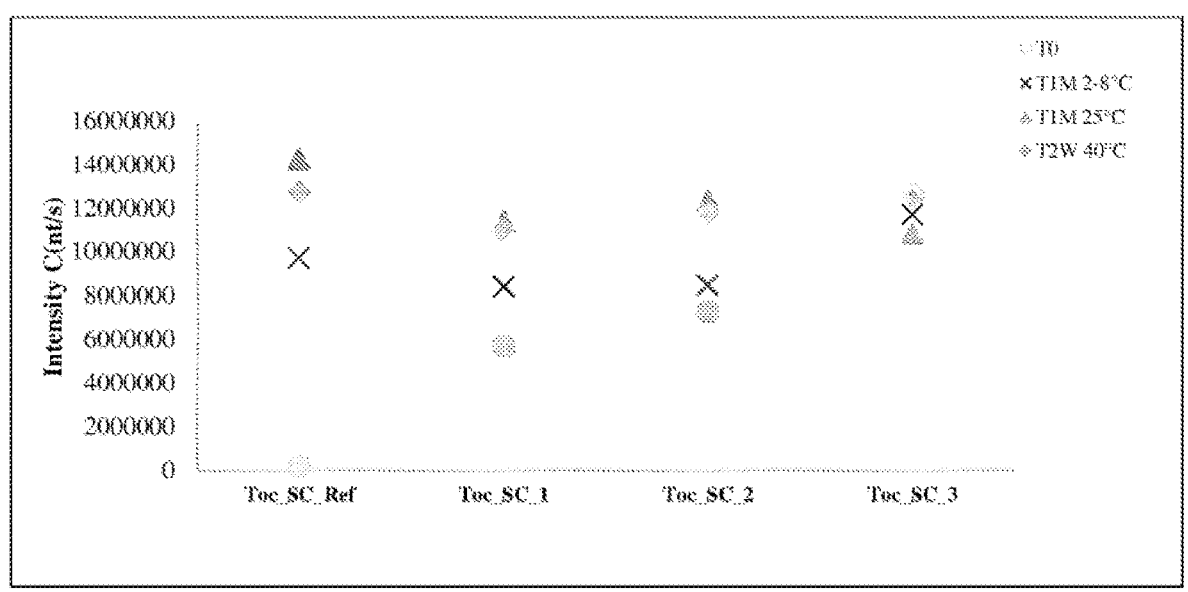
FIG. 4 illustrates differential light scattering (DLS) data, the effect of various excipients on the stability high concentration tocilizumab formulations prepared as per example 6.

Further, the said samples were also tested for colloidal stability using DLS [results are shown in FIG. 4].

TABLE 6

Tocilizumab (180 mg/ml) formulations, formulated according to Example-6

| Sample ID | Buffer combination along with different excipients |
|---|---|
| Toc mab SC-Ref | 20 mM of histidine buffer, 21 mg/mL of Arginine, 4.5 mg/mL L-Methionine, 0.2 mg/mL Polysorbate 80 (pH 6.0) |

TABLE 6-continued

Tocilizumab (180 mg/ml) formulations, formulated according to Example-6

| Sample ID | Buffer combination along with different excipients |
|---|---|
| Toc-SC-1 | 20 mM phosphate-histidine buffer, 4.5 mg/mL methionine, 40 mg/ml Sorbitol, 10 mM NaCl, 0.2 mg/mL Polysorbate 80 (pH 6.0) |
| Toc-SC-2 | 20 mM phosphate-histidine buffer, 4.5 mg/mL methionine, 40 mg/ml Sorbitol, 0.2 mg/mL Polysorbate 80 (pH 6.0) |
| Toc-SC-3 | 20 mM phosphate-histidine buffer, 30 mg/mL sorbitol, 15 mg/mL arginine, 0.2 mg/mL Polysorbate 80 (pH 6.0) |

TABLE 7

Change in pH of toclizumab formulations prepared as per example 6 at 2-8° C., 25° C. and 40° C.

| | pH of the formulation at '0' time point | Temperature | | | |
|---|---|---|---|---|---|
| Sample ID | | 2-8° C. T1M | 25° C. T1M | 40° C. T2W | T4W |
| Toc mab SC-Ref | 6.15 | 6.23 | 6.27 | 6.18 | 6.23 |
| Toc-SC-1 | 6.19 | 6.18 | 6.24 | 6.24 | 6.25 |
| Toc-SC-2 | 6.37 | 6.28 | 6.38 | 6.32 | 6.33 |
| Toc-SC-3 | 6.19 | 6.05 | 6.08 | 6.10 | 6.11 |

T-indicates time, M-months; and W-weeks

TABLE 8

Visual inspection of toclizumab formulations prepared as per example 6, at 2-8° C., 25° C. and 40° C.

| | Temperature | | | | | | | |
|---|---|---|---|---|---|---|---|---|
| | 2-8° C. | | | 25° C. | | | 40° C. | |
| Sample ID | T1 M | T3 M | T6 M | T1 M | T3 M | T6 M | T2 W | T4 W |
| Toc mab SC-Ref | Clear | Clear | Clear | Clear | Clear | Clear | Clear | Clear |
| Toc-SC-1 | Clear | Clear | Clear | Clear | Clear | Clear | Clear | Clear |
| Toc-SC-2 | Clear | Clear | Clear | Clear | Clear | Clear | Clear | Clear |
| Toc-SC-3 | Clear | Clear | Clear | Clear | Clear | Clear | Clear | Clear |

T-indicates time, M-months; and W-weeks

TABLE 9a

SEC data of toclizumab formulations prepared as per example 6, at 2-8° C.

| Sample ID | Time Point | % HMWs | % Monomer | % LMWs |
|---|---|---|---|---|
| Toc mab SC-Ref | T0 | 1.30 | 98.70 | 0.00 |
| | T1M | 1.48 | 98.50 | 0.02 |
| | T3M | 1.45 | 98.52 | 0.03 |
| | T6M | 1.58 | 98.35 | 0.07 |
| Toc-SC-1 | T0 | 1.41 | 98.59 | 0.00 |
| | T1M | 1.51 | 98.47 | 0.03 |
| | T3M | 1.60 | 98.37 | 0.03 |
| | T6M | 1.70 | 98.24 | 0.06 |
| Toc-SC-2 | T0 | 1.41 | 98.59 | 0.00 |
| | T1M | 1.58 | 98.40 | 0.02 |
| | T3M | 1.63 | 98.33 | 0.03 |
| | T6M | 1.68 | 98.25 | 0.07 |
| Toc-SC-3 | T0 | 1.38 | 98.62 | 0.00 |
| | T1M | 1.53 | 98.45 | 0.02 |
| | T3M | 1.56 | 98.41 | 0.03 |
| | T6M | 1.64 | 98.31 | 0.06 |

T-indicates time, M-months;

TABLE 9b

SEC data of toclizumab formulations prepared as per example 6, at 25° C.

| Sample ID | Time Point | % HMWs | % Monomer | % of Monomer Shoulder | % LMWs |
|---|---|---|---|---|---|
| Toc mab SC-Ref | T0 | 1.30 | 98.70 | 0.00 | 0.00 |
| | T1M | 1.39 | 98.48 | 0.00 | 0.13 |
| | T3M | 1.55 | 96.87 | 1.37 | 0.21 |
| | T6M | 1.78 | 96.03 | 1.59 | 0.61 |
| Toc-SC-1 | T0 | 1.41 | 98.59 | 0.00 | 0.00 |
| | T1M | 1.64 | 98.27 | 0.00 | 0.10 |
| | T3M | 1.86 | 96.24 | 1.67 | 0.23 |
| | T6M | 3.10 | 94.88 | 1.48 | 0.54 |
| Toc-SC-2 | T0 | 1.41 | 98.59 | 0.00 | 0.00 |
| | T1M | 1.55 | 98.34 | 0.00 | 0.11 |
| | T3M | 1.86 | 97.36 | 0.56 | 0.22 |
| | T6M | 2.53 | 95.51 | 1.47 | 0.49 |
| Toc-SC-3 | T0 | 1.38 | 98.62 | 0.00 | 0.00 |
| | T1M | 1.79 | 98.14 | 0.00 | 0.07 |
| | T3M | 1.91 | 96.33 | 1.57 | 0.18 |
| | T6M | 2.61 | 95.80 | 1.18 | 0.41 |

T-indicates time, M-months;

TABLE 9c

SEC data of toclizumab formulations prepared as per example 6, at 40° C.

| Sample ID | Time Point | % HMWs | % Monomer | % of Monomer Shoulder | % LMWs |
|---|---|---|---|---|---|
| Toc mab SC-Ref | T0 | 1.30 | 98.70 | 0.00 | 0.00 |
| | T2W | 1.30 | 98.50 | 0.00 | 0.20 |
| | T4W | 1.78 | 96.39 | 1.35 | 0.49 |
| Toc-SC-1 | T0 | 1.41 | 98.59 | 0.00 | 0.00 |
| | T2W | 1.58 | 98.30 | 0.00 | 0.12 |
| | T4W | 2.30 | 96.12 | 1.18 | 0.40 |
| Toc-SC-2 | T0 | 1.41 | 98.59 | 0.00 | 0.00 |
| | T2W | 1.61 | 98.24 | 0.00 | 0.15 |
| | T4W | 2.37 | 96.00 | 1.22 | 0.41 |
| Toc-SC-3 | T0 | 1.38 | 98.62 | 0.00 | 0.00 |
| | T2W | 1.48 | 98.36 | 0.00 | 0.16 |
| | T4W | 2.07 | 96.35 | 1.17 | 0.41 |

T-indicates time, M-months;

Example 7

Stable Tocilizumab Formulations (180 mg/ml) Devoid of Anti-Oxidants

In general, oxidation, specifically, oxidation of methionine residues generates basic variants and elutes as a basic peak (i.e., later than the main peak) during an IEX chromatography. From, the above experiment, tocilizumab formulations containing sorbitol and arginine were most stable as compared to formulations which does not contain arginine. Further, various concentrations of sorbitol and arginine containing tocilizumab formulations without any anti-oxidant (methionine) were evaluated for the formation of basic species. Details of the formulations are given in Table 10. All the samples were subjected for stability studies at 2-8° C., 25° C. and 40° C. The samples were withdrawn periodically at different time points and analyzed for acidic, basic and main peak content using IEX chromatography [results are shown Table 11 a-c].

TABLE 10

Tocilizumab (180 mg/ml) formulations, formulated according to Example-7

| Sample ID | Buffer combination along with different excipients |
|---|---|
| Toc mab SC-Ref | 20 mM of histidine buffer, 21 mg/mL of Arginine, 4.5 mg/mL L-Methionine, 0.2 mg/mL Polysorbate 80 (pH 6.0) |
| Toc-SC-3 | 20 mM phosphate-histidine buffer, 30 mg/mL sorbitol, 15 mg/mL arginine, 0.2 mg/mL Polysorbate 80 (pH 6.0) |
| Toc-SC-4 | 20 mM phosphate-histidine buffer, 15 mg/mL sorbitol, 10 mg/mL arginine, 0.2 mg/mL Polysorbate 80 (pH 6.0) |
| Toc-SC-5 | 20 mM phosphate-histidine buffer, 10 mg/mL sorbitol, 15 mg/mL arginine, 0.2 mg/mL Polysorbate 80 (pH 6.0) |

TABLE 11a

IEX data of toclizumab formulations prepared as per example 7, at 2-8° C.

| Sample ID | Time Point | % Acidic | % Main peak | % Basic |
|---|---|---|---|---|
| Toc mab SC-Ref | T0 | 18.80 | 75.21 | 5.99 |
|  | T1M | 18.59 | 75.61 | 5.80 |
|  | T3M | 19.05 | 76.60 | 4.35 |
| Toc-SC-3 | T0 | 18.54 | 75.28 | 6.18 |
|  | T1M | 18.68 | 75.96 | 5.36 |
|  | T3M | 19.31 | 76.36 | 4.34 |
| Toc-SC-4 | T0 | 18.87 | 75.04 | 6.09 |
|  | T1M | 18.62 | 76.26 | 5.11 |
|  | T3M | 19.17 | 76.57 | 4.26 |
| Toc-SC-5 | T0 | 18.96 | 74.54 | 6.50 |
|  | T1M | 18.61 | 76.42 | 4.97 |
|  | T3M | 19.20 | 76.27 | 4.54 |

T-indicates time, M-months;

TABLE 11b

IEX data of toclizumab formulations prepared as per example 6, at 25° C.

| Sample ID | Time Point | % Acidic | % Main peak | % Basic |
|---|---|---|---|---|
| Toc mab SC-Ref | T0 | 18.80 | 75.21 | 5.99 |
|  | T1M | 20.56 | 74.44 | 5.00 |
|  | T3M | 25.16 | 69.98 | 4.87 |
| Toc-SC-3 | T0 | 18.54 | 75.28 | 6.18 |
|  | T1M | 20.29 | 74.52 | 5.18 |
|  | T3M | 24.98 | 69.85 | 5.17 |
| Toc-SC-4 | T0 | 18.87 | 75.04 | 6.09 |
|  | T1M | 19.37 | 74.53 | 6.09 |
|  | T3M | 25.10 | 69.25 | 5.65 |
| Toc-SC-5 | T0 | 18.96 | 74.54 | 6.50 |
|  | T1M | 20.09 | 74.74 | 5.17 |
|  | T3M | 23.53 | 70.00 | 6.47 |

T-indicates time, M-months;

TABLE 11c

IEX data of toclizumab formulations prepared as per example 7 at 40° C.

| Sample ID | Time Point | % Acidic | % Main peak | % Basic |
|---|---|---|---|---|
| Toc mab SC-Ref | T0 | 18.80 | 75.21 | 5.99 |
|  | T2W | 24.08 | 69.41 | 6.51 |
|  | T4W | 31.54 | 62.51 | 5.95 |
| Toc-SC-3 | T0 | 18.54 | 75.28 | 6.18 |
|  | T2W | 26.77 | 66.59 | 6.64 |
|  | T4W | 33.76 | 59.64 | 6.61 |
| Toc-SC-4 | T0 | 18.87 | 75.04 | 6.09 |
|  | T2W | 26.15 | 66.49 | 7.36 |
|  | T4W | 33.84 | 59.98 | 6.18 |
| Toc-SC-5 | T0 | 18.96 | 74.54 | 6.50 |
|  | T2W | 26.05 | 67.36 | 6.59 |
|  | T4W | 33.29 | 60.27 | 6.44 |

T-indicates time, W-weeks;

Example-8

Formulations of Tocilizumab (20 mg/ml) in Phosphate-Amino Acid Based Dual Buffer System Comprising Different Excipients As part of experimental design, to formulate low concentration of tocilizumab (20 mg/ml), various 'phosphate-amino acid' buffers were prepared in 20 mM concentrations to which different excipients such as sugars/polyols, surfactants were added. Optionally, salt viz., sodium chloride, was added to the some of the 'phosphate-amino acid' buffer combinations. Tocilizumab (at concentration 30.02 mg/ml) obtained from final downstream process step was buffer exchanged into different dual buffer systems comprising phosphate-amino acid buffers and pharmaceutically acceptable excipients [composition as provided in Table 12]. The samples were then diluted/adjusted in the respective buffer back ground containing excipients to achieve a concentration of 20 mg/ml of tocilizumab. Tocilizumab formulated in buffer composition comprising phosphate buffer, sucrose and polysorbate 80, served as a reference standard, since the approved formulation of 20 mg/ml of Actemra® or Roactemra® is in this buffer composition.

TABLE 12

Tocilizumab (20 mg/ml) formulated in different dual buffer combinations according to Example-8

| Sample-ID | Buffer combination along with different excipients |
|---|---|
| Toc-Ref | 15 mM Phosphate buffer, Sucrose (50 mg/ml), polysorbate 80 (0.5 mg/ml) at pH 6.5 |
| Toc-IV1 | 20 mM Phosphate-Histidine, Sucrose (60 mg/ml), polysorbate 80 (0.5 mg/ml) at pH 6.0 |
| Toc-IV2 | 20 mM Phosphate-Succinate, Sorbitol (50 mg/ml), polysorbate 80 (0.5 mg/ml) at pH 6.0 |
| Toc-IV3 | 20 mM Phosphate-Glycine, Sorbitol (50 mg/ml), polysorbate 80 (0.5 mg/ml) at pH 6.0 |
| Toc-IV4 | 20 mM Phosphate-Glutamate, Sorbitol (50 mg/ml), polysorbate 80 (0.5 mg/ml) at pH 6.0 |
| Toc-IV5 | 20 mM Phosphate-Histidine, Sorbitol (10 mg/ml), 15 mM NaCl, polysorbate 80 (0.5 mg/ml) at pH 6.5 |
| Toc-IV6 | 20 mM Phosphate-Histidine, Sorbitol (30 mg/ml), polysorbate 80 (0.5 mg/ml) at pH 6.0 |

The tocilizumab formulations, mentioned in Table-6, were subjected for accelerated stability conditions at 40° C. for 4 weeks. The formulations were thereafter analyzed for high molecular weight species and monomeric content using size exclusion chromatography (SEC) and the results are shown in Table-13. Percentage of acidic species and main peak content were analyzed using ion-exchange chromatography (IEX) and results of the same are shown in Table-14.

TABLE 13

SEC data of tocilizumab (20 mg/ml) formulations, formulated as per Example-8, and stored at 40° C. for 4 weeks

| Sample-ID | % of HMW at 40° C. at 0 week | | % of Monomer content at |
|---|---|---|---|
| | 0 week | 4$^{th}$ week | 40° C. at 4 weeks |
| Toc-Ref | 1.3 | 2.1 | 97.4 |
| Toc-IV1 | 1.3 | 1.7 | 97.7 |
| Toc-IV2 | 0.9 | 3.3 | 92.1 |
| Toc-IV3 | 1.3 | 1.9 | 97.6 |
| Toc-IV4 | 1.1 | 2.0 | 97.5 |
| Toc-IV5 | 0.2 | 0.3 | 98.0 |
| Toc-IV6 | 0.1 | 0.2 | 97.9 |

TABLE 14

IEX data of tociliziuamb (20 mg/ml) formulations, formulated as per Example-8, and stored at 40° C. for 4 weeks

| Sample-ID | % of basic species at 40° C. at 4 weeks | % of main peak content at 40° C. at 4 weeks |
|---|---|---|
| Toc-Ref | 8.0 | 52.9 |
| Toc-IV1 | 10.9 | 44.8 |
| Toc-IV2 | 7.1 | 33.8 |
| Toc-IV3 | 8.4 | 52.3 |
| Toc-IV4 | 9.3 | 52.0 |
| Toc-IV5 | 4.8 | 59.9 |
| Toc-IV6 | 5.8 | 56.2 |

Tocilizumab formulations, formulated as per Table-12 were subjected to accelerated stability studies, and checked for visual inspection [results are shown in table 15].

TABLE 15

Visual inspection data of tocilizumab (20 mg/ml) formulations, formulated according to Example-8.

| Sample-ID | Visual inspection at 40° C. | | |
|---|---|---|---|
| | 0 week | 2 weeks | 4 weeks |
| Toc-Ref | Clear | Clear | Clear |
| Toc-IV1 | Clear | Clear | Clear |
| Toc-IV2 | Clear | Turbid | Turbid |
| Toc-IV3 | Clear | Clear | Clear |
| Toc-IV4 | Clear | Clear | Slight turbid |
| Toc-IV5 | Clear | Clear | Clear |
| Toc-IV6 | Clear | Clear | Clear |

Example 9

Other Antibodies Formulated in Phosphate-Amino Acid Dual Buffer Back Ground 21 mg/ml of trastuzumab (Tmab) was formulated in single as well as dual buffer. Details of the formulations are given in Table 16.

TABLE 16

Trastuzumab composition in single buffer and dual buffer

| Sample ID | Formulation details |
|---|---|
| Tmab-His buffer, pH 5.5 | Trastuzumab, Histidine buffer, Trehalose, methionine and polysorbate |
| Tmab-His-Phos buffer, pH 5.5 | Trastuzumab, Histidine-phosphate buffer, Trehalose, methionine and polysorbate |

The above samples were subjected were subjected for accelerated stability studies by keeping the said samples at 37° C. for 4 weeks. Further, the samples were tested for change in pH (results are shown in Table 17).

TABLE 17 pH measurements of T-mab formulations prepared as per example 7, at 37° C.

| Sample ID | pH at 37° C. | | |
|---|---|---|---|
| | 0 week | 2 weeks | 4 weeks |
| Tmab in His buffer | 5.4 | 5.5 | 5.8 |
| Tmab in His-Phos buffer | 5.5 | 5.6 | 5.6 |

The invention claimed is:

1. A stable liquid tocilizumab formulation, consisting of tocilizumab, a phosphate-amino acid dual buffer system and one or more pharmaceutically acceptable excipients, and wherein the concentration of the antibody stabilized is from about 10 mg/ml to about 200 mg/ml; the amino acid is selected from the group consisting of histidine, glycine, and aspartate, and the excipients are selected from the group consisting of sorbitol, arginine and polysorbate.

2. The formulation according to claim 1, wherein the tocilizumab formulated in the phosphate-amino acid buffer remains stable under one of the following storage conditions at 2-8° C. for at least 6 months or at 25° C. for at least 6 months, or at 40° C. for at least 2 weeks.

3. The formulation according to claim 1, wherein the amino acid acts as counter ion to the phosphate component of the buffer in the formulation.

4. The formulation according to claim 1, wherein the formulation has a viscosity of less than 10 cp.

5. The formulation according to claim 1, wherein the concentration of buffer in the said formulation is less than 100 mM.

6. The formulation according to claim 1, wherein the formulation does not contain anti-oxidants.

7. A stable liquid formulation of tocilizumab according to claim 1, wherein the formulation maintains at least 95% of monomeric content and/or contains less than 5% of aggregates of the antibody, after storage at 2-8° C. for at least 6 months or at 25° C. for at least 6 months, or at 40° C. for at least 2 weeks.

8. The formulation according to claim 1, wherein the formulation does not contain methionine.

* * * * *